United States Patent [19]

Misaki et al.

[11] Patent Number: 4,767,712
[45] Date of Patent: Aug. 30, 1988

[54] ASSAY METHOD USING NAD SYNTHETASE AND A PROCESS FOR PRODUCTION OF THE ENZYME

[75] Inventors: Hideo Misaki; Hidehiko Ishikawa; Kazuo Matsuura, all of Shizuoka, Japan

[73] Assignee: Toyo Jozo Kabushiki Kaisha, Shizuoka, Japan

[21] Appl. No.: 603,710

[22] Filed: Apr. 25, 1984

[30] Foreign Application Priority Data

Apr. 25, 1983 [JP]  Japan .................................. 58-71513

[51] Int. Cl.$^4$ ............................ C12N 1/20; C12R 1/10
[52] U.S. Cl. ...................................... 435/253; 435/836
[58] Field of Search .................... 435/4, 15, 16, 17, 18, 435/25, 26, 183, 836, 253

[56]  References Cited

U.S. PATENT DOCUMENTS

| 4,318,980 | 3/1982 | Boguslaski et al. | 435/7 |
| 4,427,771 | 1/1984 | Misaki et al. | 435/26 |

FOREIGN PATENT DOCUMENTS

| 1129316 | 8/1982 | Canada | 435/15 |
| 2743 | 3/1983 | Fed. Rep. of Germany . | |
| 59-31696 | 2/1984 | Japan | 435/4 |

OTHER PUBLICATIONS

Bergmeyer, *Methods of Enzymatic Analysis*, vol. 1, 4, 2nd Ed. Academic Press, Inc., New York, 131-144, 1909, 1919 (1974).
Yu et al., Chemical Abstracts, 77: 110798p, 154 (1972).
Preiss et al., J. Biol. Chem., 233(2): 493-500 (1958).
Imsande et al., J. Biol. Chem., 236(2): 525-530 (1961).
Yu et al., J. Biol. Chem., 237: 4794-4802 (1972).
Imsande et al., J. Biol. Chem., 236: 1494-1497 (1961).
Spencer et al., J. Biol. Chem., 242(3): 385-392 (1967).

*Primary Examiner*—Esther M. Kepplinger
*Attorney, Agent, or Firm*—Young & Thompson

[57]  ABSTRACT

An assay method for a component in a specimen containing any one of ATP, deamide-NAD and an amide donor which comprises performing a main reaction which comprises incubating the specimen with NAD synthetase in the presence of ATP, deamide-NAD, an amide donor and $Mg^{++}$ to generate NAD; performing a coenzyme-cycling reeaction by combining the oxidation-reduction reaction system with coenzyme NAD and the oxidation-reduction reaction system with coenzyme reduced NAD, and measuring a consumed or generated component in the cycling reaction. The NAD synthetase can be produced by culturing the microorganism *Bacillus licheniformis* B-0844 FERM P-6809, in a culture medium, and isolating the thus-produced NAD synthetase therefrom.

1 Claim, 3 Drawing Sheets

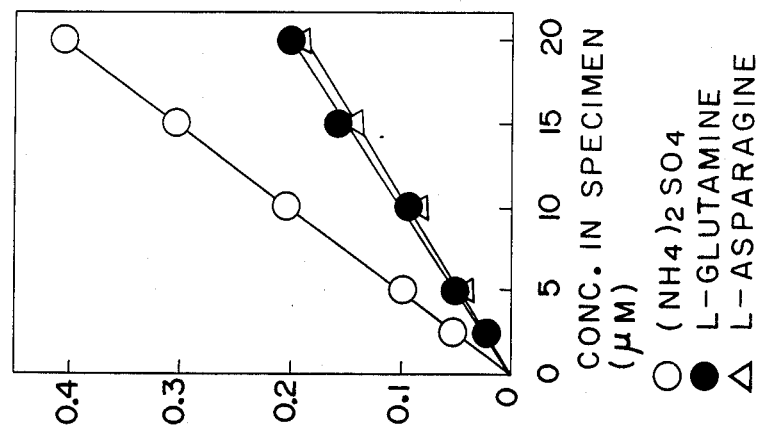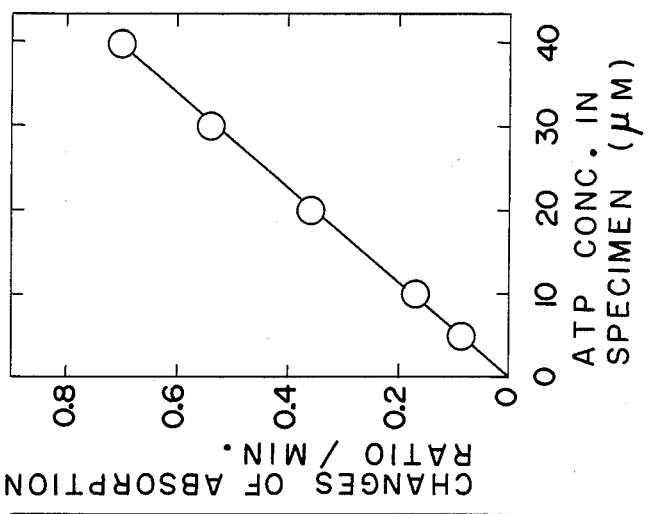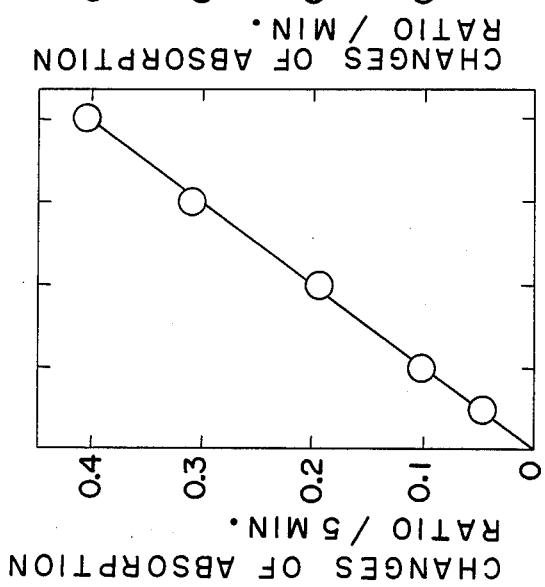

ASSAY METHOD USING NAD SYNTHETASE AND A PROCESS FOR PRODUCTION OF THE ENZYME

This invention relates to an assay method using NAD synthetase, and to a process for the production of the said enzyme.

More particularly, the present invention relates to an assay method of a component in a specimen said component being selected from ATP, deamide-NAD and an amide donor, which comprises, as a main reaction step, incubating the specimen containing ATP, deamide-NAD or an amide donor such as $NH_3$, L-glutamine (hereinafter designated L-Gln) or L-asparagine (hereinafter designated L-Asn), with NAD synthetase in the presence of ATP, deamide-NAD, an amide donor and $Mg^{++}$ to generate NAD. A coenzyme cycling reaction is also performed, by combining the oxidation-reduction reaction system with coenzyme NAD and the oxidation-reduction reaction system with coenzyme reduced NAD. A consumed or generated component in the said cycling reaction is then measured, to effect the assay.

Heretofore, NAD synthetase has been known to exist in rat liver [J. Biol. Chem., 233, 493–500 (1958)], porcine liver [ibid., 236, 525–530 (1961)], yeast [ibid., 247, 4794–4802 (1972)] and E. coli [ibid., 236, 1494–1497 (1961) and 242, 385–392 (1967)].

The said NAD synthetase is classified as NAD synthetase (EC 6.3.1.5) which catalyses a reaction:

$$ATP + \text{deamide-NAD} + NH_3 \underset{}{\overset{Mg^{++}}{\rightleftarrows}} AMP + PPi + NAD$$

and NAD synthetase (EC 6.3.5.1) which catalyses a reaction:

$$ATP + \text{deamide-NAD} + \text{L-Gln} + H_2O \underset{}{\overset{Mg^{++}}{\rightleftarrows}} AMP + PPi + NAD + \text{L-glutamate}$$

These NAD synthetases utilize $NH_3$ or an amide of L-Gln, and are differentiated by the inhibitory action of azaserine.

An assay method of NAD synthetase has been reported, in which the generated NAD is reduced by alcohol dehydrogenase (EC 1.1.1) and the absorbancy of the generated reduced NAD (hereinafter designated NADH) is spectrophotometrically measured at 340 nm or the generated NAD is measured by fluorometry. However, ATP, deamide-NAD, $NH_3$ or L-Gln cannot be measured by this known method, due to the low sensitivity of the enzyme activity.

We have found that the consumed or generated component thereof can be measured by an amplified reaction system comprising a coenzyme cycling reaction, by combining the oxidation-reduction reaction system with generated NAD as a coenzyme from the NAD synthetase reaction hereinabove, and the oxidation-reduction reaction system with NADH as a coenzyme.

The present invention therefore relates to an assay method of a component in a specimen said component being selected among ATP, deamide-NAD and an amide donor, which comprises incubating the specimen with NAD-synthetase in the presence of ATP, deamide-NAD, an amide donor and $Mg^{++}$ to generate NAD, and performing a coenzyme cycling reaction by combining the oxidation-reduction reaction system with coenzyme NAD and the oxidation-reduction reaction system with coenzyme NADH. A consumed or generated component in the said cycling reaction is then measured, to effect the assay.

In the accompanying drawings:

FIG. 4 is the curve of ATP assay by the endpoint method.

FIG. 5 is the curve of ATP assay by the kinetics method.

FIG. 6 is the curve of L-glutamine and L-asparagine assay by the endpoint method.

Figure 1:
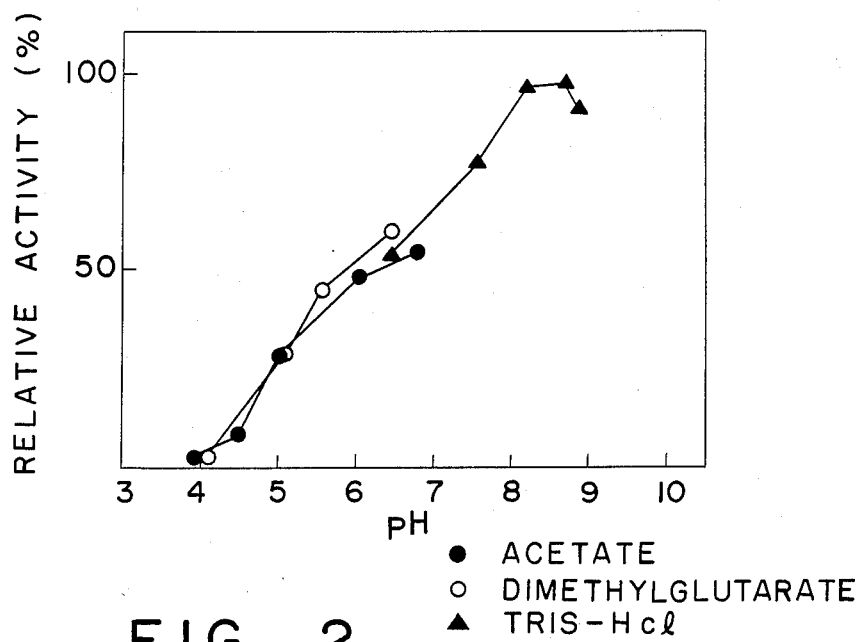
FIG. 1 is the curve of optimum pH of NAD synthetase from Bacillus licheniformis B-0844.

The reaction system of the present invention can be summarized as follows:

(1) Main reaction system:

Utilizing $NH_3$ as an amide donor:

ATP + deamide-NAD +

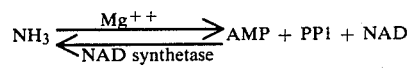

Utilizing Gln or Asn as an amide donor:

ATP + deamide-NAD + L-Gln (L-Asn) +

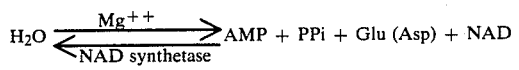

(2) Coenzyme cycling reaction system:

(a) oxidation-reduction reaction system with coenzyme NAD;

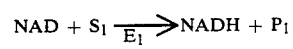

(b) transfer reaction system with coenzyme NADH;

wherein;

$NH_3$: compound containing monovalent ammonium ion, $E_1$: dehydrogenase which catalyzes a reaction consuming the substrates NAD and $S_1$, and generating NADH and $P_1$, $E_2$: active substance which catalyzes a reaction consuming NADH and $S_2$, and generating NAD and $P_2$, $S_1$: reduced substrate in $E_1$, $S_2$: oxidized substrate in $E_2$, $P_1$: oxidation product of $S_1$, $P_2$: reduction product of $S_2$.

A reaction utilizing $NH_3$ is illustrated as follows:

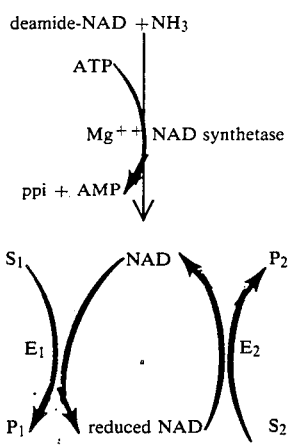

An example of a specimen is one containing at least a substrate of the main reaction system hereinbefore, i.e. ATP, deamide-NAD or an amide donor, for example a specimen originally containing one component of the said substrate, or a specimen containing the substrate which is generated or consumed by another enzyme reaction system.

A preferred example of the above enzyme reaction system is a reaction system which consumes or generates ATP, $NH_3$ or an amide donor of L-Gln or L-Asn, without the coenzymes NAD and NADH, as in the following non-limitative examples:

(1) Enzymatic reaction systems which generate ATP:
 (1) creatine kinase (EC 2.7.3.2):

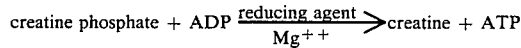

reducing agent: β-mercapto ethanol, reduced glutathione, cysteine, N-acetylcysteine, dithiothreitol, etc.
 (2) pyruvate kinase (EC 2.7.1.40):

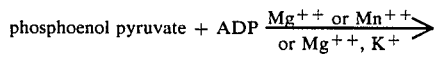

pyruvate + ATP (3) acetate kinase (EC 2.7.2.1):

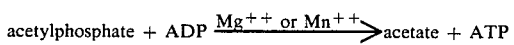

(4) carbamate kinase (EC 2.7.2.2):

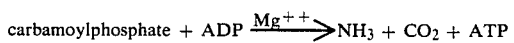

(5) aspartate kinase (EC 2.7.2.4):

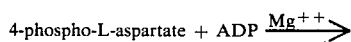

L-aspartate + ATP (6) phosphoglycerate kinase (EC 2.7.2.3):

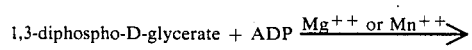

3-phospho-D-glycerate + ATP (7) arginine kinase (EC 2.7.3.3):

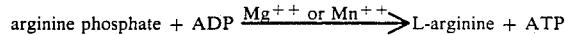

(2) Enzymatic reaction systems which utilize ammonium-generating water soluble ammonium salts or $NH_3$:
 (1) Examples of water-soluble ammonium salts are inorganic or organic ammonium salts which generate ammonium ions such as ammonium chloride, aqueous ammonia, ammonium sulfate, ammonium nitrate, ammonium acetate, ammonium citrate, etc.
 (2) nicotine amidase (EC 3.5.1.19):

nicotine amide + $H_2O$ → nicotinate + $NH_3$ + $H^+$ (3) glutamyl-peptide-glutaminase (EC 3.5.1.44):

L-glutaminyl-peptide + $H_2O$ → L-glutamyl-peptide + $NH_3$ (4) arginine deaminase (EC 3.5.3.6):

L-arginine + $H_2O$ → citrulline + $NH_3$ + $H^+$ (5) guanidine deaminase (EC 3.5.4.3):

guanine + $H_2O$ → xanthine + $NH_3$ + $H^+$ (6) adenosine deaminase (EC 3.5.4.4):

adenosine + $H_2O$ → inosine + $NH_3$ + $H^+$ (7) creatinine deaminase (EC 3.5.4.21):

creatinine + $H_2O$ → N-methylhydantoin + $NH_3$ + $H^+$ (8) threonine dehydratase (EC 4.2.1.16):

L-threonine + $H_2O$ → 2-oxobutyrate + $CO_2$ + $NH_3$ + $H^+$ (9) aspartate ammonium-liase (EC 4.3.1.1):

L-aspartate → fumarate + $NH_3$ + $H^+$

(10) L-methionine-γ-liase (EC 4.4.1.11):

L-methionine + $H_2O$ → 2-oxobutyrate + methanethiol + $NH_3$ + $H^+$

(11) methylaminoglutamate methyl transferase (EC 2.1.1.21):

N-methylglutamate + $NH_3$ + $H^+$ ⇌ glutamate + methylamine (3) Enzymatic reaction systems utilizing L-Gln:
 (1) glutamine transaminase (EC 2.6.1.15):

L-Gln + 2-oxi acid → 2-oxoglutamate + L-amino acid (2) carbamoylphosphate synthetase (EC 6.3.5.5):

L-Gln + $HCO_3^-$ + 2ATP + $H_2O$ → carbamoylphosphate + 2ADP + Pi + L-glutamate (3) hexosephosphate aminotransferase (EC 5.3.1.19):

D-fructose-6-phosphate+L-Gln→2-amino-2-deoxy-
D-glucose-6-phosphate+L-glutamate (4) glutamine-scyllo-inosose aminotransferase (EC 2.6.1.50):

2-oxoglutaramate+1-amino-1-deoxy-scyllo-
inositol→L-Gln+2,4,6/3,5-pentahydroxycy-
clohexanone (4) Enzymatic reaction systems utilizing L-Asn:
(1) asparagine transaminase (EC 2.6.1.14):

L-Asn+2-oxi-acid⇌2-oxosuccinate+L-amino acid (2) 3-cyanoalanine hydratase (EC 4.2.1.65):

3-cyanoalanine+$H_2O$→L-Asn

As hereinabove illustrated, in the present invention, not only the reaction mixture containing ATP, $NH_3$, L-Gln or L-Asn which is consumed or generated in the illustrated enzymatic reaction system, but also the reaction mixture for measuring the enzymatic activity which is used in the enzymatic reaction system, consumed substrate or generated product, can be used as a specimen to be assayed.

In these enzymatic reaction systems, ATP, $NH_3$, L-Gln or L-Asn is assayed for the purpose of determining the enzymatic activity in the said enzymatic reaction or measuring any one of the components thereof. A substance other than the component to be assayed is added at a constant rate as a reagent. The amount of the specimen or reagent can be varied depending on the objects and conditions. Generally, the reaction proceeds at 37° C. for at least one minute.

The preferred NAD synthetase used in the present invention is an enzyme derived from microorganisms such as *Escherichia coli* or *Bacillus licheniformis*, due to its stability as an enzyme for diagnosis. Particularly preferred is the enzyme of *Bacillus licheniformis* B-0844, which has been found by the present invention.

The above NAD synthetase catalyzes the reaction;

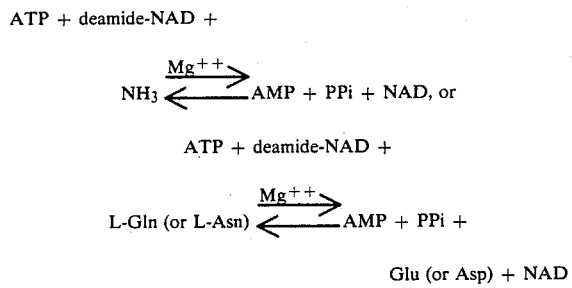

Glu (or Asp) + NAD wherein Glu is L-glutamate and Asp is L-aspartate. During the main reaction, the specimen containing one of ATP, deamide-NAD, $NH_3$ or an amide donor such as L-Gln or L-Asn, and the remaining substrates which are not to be assayed, are treated in the presence of $Mg^{++}$ with NAD synthetase.

The above enzymatic reaction is performed generally in a volume of 10 μl-3 ml per test. The amount of NAD synthetase used varies depending on the reaction time, and is generally 0.5-100 units per test. The amount of the substrates should be at least in excess for the component to be assayed. NAD is generated by the said main reaction depending upon the amount of ATP, deamide-NAD or amide donor in the specimen.

In order to achieve the correct and exact determination, an amplified reaction by coenzyme cycling is used. In this invention, NAD, which is converted and generated depending upon the amount of ATP, deamide-NAD or amide donor in the specimen, is subjected to a cycling reaction in combination with the oxidation-reduction reaction system for coenzyme NAD and that of NADH, and the consumed or generated component in the above reaction is preferably measured.

Examples of oxidation-reduction reaction systems with coenzyme NAD are reaction systems constituting dehydrogenase ($E_1$) which consumes NAD to generate NADH and its substrate ($S_1$), or dehydrogenase ($E_1$) with coenzyme NAD or NADP and its substrate ($S_1$). The source of the dehydrogenase is not limited and at least this enzyme reacts with specific substrates and consumes coenzyme NAD to form NADH.

Examples of these enzymes and substrates are mentioned in the "Enzyme Handbook". Examples are as follows:
lactate dehydrogenase (EC 1.1.1.27) and L-lactate,
alcohol dehydrogenase (EC 1.1.1) and ethanol,
glycerol dehydrogenase (EC 1.1.1.6) and glycerol,
glycerol-3-phosphate dehydrogenase (EC 1.1.1.8) and glycerol-3-phosphate,
glucose dehydrogenase (EC 1.1.47) and glucose,
malate dehydrogenase (EC 1.1.1.37) and L-malate,
glutamate dehydrogenase (EC 1.4.1.2) and L-glutamate,
3-α-hydroxysteroid dehydrogenase (EC 1.1.1.50) and 3-α-hydroxysteroid.

The amount of enzyme used in these oxidation-reduction reactions varies depending on the enzyme activity, the kind of substrate and the ratio of coenzyme cycling. The substrate should be in molar excess as compared with the cycling coenzyme, because one molar ratio of substrate is consumed per cycle, and so the amount of substrate is determined by the number of cycles per hour and the reaction time. The concentration of the substrate is preferably determined to attain a maximum reaction rate of oxido-reductase, and is 0.1 mM-100 mM.

The reaction system for coenzyme NADH is a reaction system of functional substance ($E_2$), which at least consumes NADH and generates NAD, and its substrate ($S_2$). Examples thereof are a reaction system with oxidoreductase, which at least consumes NADH and generates NAD, and its substrate, and a reaction system consisting of an electron-transfer agent and a tetrazolium salt.

Examples of oxidoreductase hereinabove are a dehydrogenase which catalyzes, with at least coenzyme NADH, a reaction or an excess amount of specific substrate ($S_2$) to form NAD and reduced substrate ($P_2$) of $S_2$; or NADH: (acceptor) oxidoreductase wherein at least NADH is the coenzyme and the acceptor is cytochrome, a disulfide compound, quinone and its analogues, but the origin is not limited. These enzymes, substrates and acceptors are mentioned in "Enzyme Handbook".

Examples of dehydrogenase and its substrate are
lactate dehydrogenase (EC 1.1.1.27) and pyruvate,
alcohol dehydrogenase (EC 1.1.1) and acetaldehyde,
glycerol dehydrogenase (EC 1.1.1.6) and dihydroxyacetone glycerol-3-phosphate dehydrogenase and dihydroxyacetonephosphate,
malate dehydrogenase and oxaloacetate; and 3-α-hydroxysteroid dehydrogenase and 3-ketosteroid.

Examples of NADH: (acceptor) oxidoreductase are cytochrome $b_5$ reductase (EC 1.6.2.2) and diaphorase.

Examples of acceptors are methylene blue, flavins, quinones and 2,6-dichlorophenol indophenol.

The combination of NADH: (acceptor) oxidoreductase and acceptor is not limited to an enzyme with coenzyme NADH and an electron acceptor, and is preferably diaphorase (EC 1.6.4.3) and tetrazolium salt, and methylene blue, NAD dehydrogenase (EC 1.6.99.3) and cytochrome c. The concentration thereof is usually 0.05-100 U/ml. The concentration of the tetrazolium salt depends upon the solubility of the tetrazolium salt and the ultimately generated formazane, and is generally 1-100 μg per one ml of reagent.

Examples of electron transfer agents are substances which have an activity for oxidizing NADH to NAD without detrimental effect on coenzyme cycling, for example phenazine methosulfate, meldola blue or pyrocyanine. The concentration thereof depends on the cycling ratio and is 5 μg-0.5 mg per ml of reaction mixture.

The above cycling reaction is carried out usually at room temperature to 37° C., preferably at 30°-37° C. The reaction time is not limited but is usually at least one minute, preferably at least 5 minutes. The reaction can be terminated by adding an acid such as hydrochloric acid or phosphoric acid.

After terminating the cycling reaction, the consumed or generated substance in the cycling reaction is measured. Examples thereof are the reduction product ($P_1$) from the reduced substrate ($S_1$) of $E_1$, or the reduced product ($P_2$) from the oxidized substrate ($S_2$) of $E_2$ as a generated component, and the reduced substrate ($S_1$) of $E_1$ or the oxidized substrate ($S_2$) of $E_2$. One of components $P_1$, $P_2$, $S_1$ or $S_2$ is measured. Most preferably, the product which is colorless as substrate and is colored or fluorescent as product, is colorimetrically measured by absorbency changes. For example, formazane generated from substrate ($S_2$) tetrazolium is reduced to form a reduced product ($P_2$) which is measured colorimetrically. Furthermore, when flavins or quinones are used as substrate ($S_2$), the consumed amount of the substrate ($S_2$) is preferably measured by colorimetry.

In the above reaction, a surface active agent is preferably added for preventing the precipitation of formazane from tetrazolium salt. Examples of surface active agents are nonionic surface active agents such as Triton X-100 (iso-octyl phenoxy polyethoxy ethanol, Rohm & Haas Co., USA) or Adekatol SO-145 (ethoxylate of secondary alcohol, Asahidenka Kogyo Co., Japan). The concentration thereof is 0.01-3% for a reagent. Adding a surface active agent provides an increased sensitivity of measurement and stability of formazane pigment.

The colorimetric assay of the generated formazane pigment can be performed by measuring the optical density (OD) at its specific absorption wavelength such as at 500-550 nm.

In the method of the present invention, an assay method such as an end-point method, a rate assay method or a dry-chemical method (film method, immobilized solid) can advantageously be used.

The method of the present invention is useful for highly sensitive assays for ATP, and can be used for measuring liberated ATP in a specimen, generated ATP from ADP in an enzymatic reaction with kinase, ADP and a phosphorus compound of a substrate for kinase, for kinase activity assay, and for assaying any one component of ADP or a phosphorus compound of a substrate for kinase or a product of kinase reaction.

Furthermore, the method of the present invention is useful for highly sensitive assays for $NH_3$, and can be used for measuring liberated $NH_3$ in specimens, generated or consumed $NH_3$ in enzymatic reactions on substrates for $NH_3$-generating enzyme action, the enzymatic activity of $NH_3$-generating enzymes, and any one of the components of substrates for $NH_3$-generating enzymes or products of $NH_3$-generating enzymatic reactions.

Furthermore, the method of the present invention is useful for highly sensitive assays for L-Gln or L-Asn, and can be used for measuring liberated L-Gln or L-Asn, generated or consumed L-Gln or L-Asn in enzymatic reactions on substrates for L-Gln- or L-Asn-generating enzyme action, the enzymatic activity of L-Gln- or L-Asn-generating enzymes, or any one of the component of substrates for Gln- or Asn-generating enzymes or the products thereof.

NAD synthetase used in the present invention obtained from *Bacillus licheniformis* B-0844 has been discovered by the inventors of the present invention, and is more stable than the known NAD synthetases and is useful as a clinical diagnostic enzyme.

Therefore, the present invention also includes a process for the production of NAD synthetase which comprises culturing a NAD synthetase-producing microorganism belonging to genus Bacillus in a culture medium, and isolating the thus-produced NAD synthetase from the cultured medium.

A strain *Bacillus licheniformis* B-0844 was isolated from a soil sample obtained in Ohno, Shuzenji-cho, Tagata-gun, Shizuoka-ken, Japan, and the taxonomical properties are as follows:

A. Morphological properties:

Observed by microscope on nutrient agar slant medium at 30° C. for 18-24 hours cultivation.

1. Form and arrangement: Round edges, straight or slightly curved bacilli, single or binary chains, rarely short chains.
2. Size: 0.6-0.8×1.5-3.0 μm.
3. Motility: motile by peritrichous flagella.
4. Spores: forms center or subterminal, 0.8×1.5 μm, swelling the sporangia.

B. Growth on various media (at 50° C.):

1. Nutrient agar plate: Colonies grayish white, undulated round edges, plain. Sometimes wrinkled. No soluble pigment formation.
2. Nutrient agar slant: Echinulate, good growth. Grayish white. No soluble pigment formation.
3. Bouillon agar: Uniformly turbid, good growth. Later forms pellicle. Villous precipitation.
4. BCP milk: Coagulates within 1-2 weeks, partial peptonization.

C. Physiological properties (+: positive, −: negative):

| | |
|---|---|
| Gram's stain | + |
| catalase production | + |
| oxidase production | + |
| urease formation | |
| (SSR medium) | − |
| (Chris. medium) | − |
| gelatin hydrolysis | + |
| starch hydrolysis | + |
| casein hydrolysis | − (3 days) |
| esculin hydrolysis | + |
| cellulose hydrolysis | − |

| -continued | |
|---|---|
| indole production | − |
| H₂S production | + |
| acetoin production | + |
| MR test | + (week) |
| nitrate reduction | + |
| denitrification reaction | − |
| citrate utilization | + |
| growth on 7.0% NaCl added medium | + |
| growth at 50° C. | + |
| growth at 20° C. | + | acid formation from sugar* (no gas formation:

| | | | |
|---|---|---|---|
| adonitol | − | mannose | + |
| L(+)arabinose | + | melezitose | − |
| cellobiose | + | melibiose | + |
| dulcitol | − | raffinose | + |
| meso-erythritol | − | L(+)rhamnose | + |
| fructose | + | salicine | + |
| fucose | − | L-sorbose | − |
| galactose | + | sorbitol | + |
| glucose | + | starch | + |
| glycerin | + | saccharose | + |
| inositol | + | trehalose | + |
| inulin | − | xylose | + |
| lactose | + | | |
| maltose | + | | |
| mannitol | + | | |

| OF test (Hucker's method) | NT (no change) |
|---|---|
| OF test (modified)* | F (fermentation) |

Carbon utilization test:

| | | | |
|---|---|---|---|
| D-alanine | − | sucrose | + |
| L-alanine | + | cellobiose | − |
| fructose | − | L(+)arabinose | − |
| propanol | − | mannose | + |
| ethanol | − | maltose | + |
| ethylamine | − | rhamnose | − |
| lactate | + | trehalose | + |
| α-aminobutyrate | − | acetate | − |
| glucose | + | propionate | + |
| inositol | − | | |

*basal medium:

| | | | |
|---|---|---|---|
| (NH₄)₂HPO₄ | 1.0 g | KCl | 0.2 g |
| MgSO₄ 7H₂O | 0.2 g | yeast ex | 1.0 g |
| Agar | 3.0 g | BTB | 0.02 g |
| Distilled water | 1000 ml | pH | 7.0 |

Cytosine and guanine contents of DNA (%): 45.6% (Tm method)

According to the above taxonomical properties, the strain B-0844 can be grown at 50° C. and is a bacterium having the characteristics of round edges, straight or slightly curved bacilli, Gram-positive, sporulating and fermentative degradation of sugar. Comparing these taxonomical properties with "Bergey's Manual", 8th Ed., 1974, "Manual of Medicinal Bacteriology", 2nd Ed., 1974 and "Agriculture Handbook", p. 427, "The genus Bacillus", the present strain is characterized by spore formation and aerobical growth and as so is referred to as genus Bacillus. Among the strains belonging to genus Bacillus which can grow at 50° C., (a) *Bacillus coagulance*, (b) *Bacillus licheniformis*, (c) *Bacillus subtilis*, (d) *Bacillus brevis* and (e) *Bacillus stearothermophilus* can be mentioned. The comparison of these strains is as follows: [+: positive, −: negative, d: different in strain]

| | B-0844 | (a) | (b) | (c) | (d) | (e) |
|---|---|---|---|---|---|---|
| Growth at 50° C. | + | + | + | + | + | + |
| Growth at 20° C. | + | + | + | + | + | − |
| Anaerobical growth | + | + | + | − | − | − |
| Utilization of propionate | + | − | + | − | − | − |
| Growth of 7% NaCl media | + | − | + | + | − | − |
| Growth of 5% NaCl media | + | + | + | + | − | d |

| -continued | | | | | | |
|---|---|---|---|---|---|---|
| | B-0844 | (a) | (b) | (c) | (d) | (e) |
| Utilization of citrate | + | d | + | + | d | d |

The present strain resembles with *Bacillus licheniformis* and so is referred to as *Bacillus licheniformis* B-0844. The strain has been deposited in the Fermentation Institute, Agency of Industrial Science and Technology, M.I.T.I., Japan and assigned No. FERM P-6809.

In the present invention, among the NAD synthetase producing microorganisms belonging to genus Bacillus, the above strain is an example, but any strain which belongs to genus Bacillus and produces NAD-synthetase can be used.

An NAD-synthetase-producing microorganism belonging to genus Bacillus is cultured in a conventional medium for enzyme production. Cultivation is carried out in liquid or solid culture and submerged aeration culture is preferred for industrial production.

The nutrient sources of the medium can be conventional media for microorganism cultivation. Examples of carbon sources are assimilable carbon compounds, and are glucose, sucrose, lactose, maltose, starch, dextrin, molasses or glycerin. Examples of nitrogen sources are assimilable nitrogen sources such as corn steep liquor, soybean powder, cotton seed powder, wheat gluten, peptone, meat extract, yeast extract or casein hydrolyzate. Salts such as magnesium, potassium, sodium, zinc, iron, manganese, and phosphates or halogens, can be used.

The culturing temperature can be chosen for the growth of NAD-synthetase-producing microorganisms and the production of the enzyme, and is preferably 26°–50° C. The culturing time can be varied depending on the culturing conditions, and is generally 15–40 hours. Cultivation should naturally be stopped upon the maximum production of enzyme. The aeration agitation is usually 200–400 r.p.m.

Since the enzyme is an endo-enzyme, the cultured cells are collected by means of filtration or centrifugation, and the collected cells are mechanically disrupted by ultrasonication. French pressing or glass-beads treatment, or enzymatically digested by lysozyme, with the addition, if necessary, of surface active agents such as Triton X-100 (iso-octyl phenoxy polyethoxy ethanol, Rohm & Haas Co., USA) or Adekatol SO-120 (ethoxylate of secondary alcohol, Asahidenka Kogyo Co., Japan).

The enzyme solution is, with or without concentration, subjected to salting-out by adding soluble salts such as ammonium sulfate, or treated by adding a water-miscible organic solvent such as methanol, ethanol, acetone or isopropanol to precipitate the enzyme. The precipitate is dissolved in water or a buffer solution, dialyzed if necessary, and chromatographed by an ion exchange resin such as DEAE-Sephadex, DEAE-Sepharose, carboxy methyl cellulose, carboxymethyl Sepharose or carboxy methyl Sephadex, or by gel-filtration using a molecular sieve such as Sephadex G-200, Sephadex CL-6B or Sephacryl S-200 (trade names).

The biochemical properties of the above NAD synthetase are as follows:

(1) Molecular weight: approximately 62,000 (gel-filtration by Sephadex G-150)

(2) Isoelectric point: approximately pH 4.6 (electrophoresis using Ampholite)

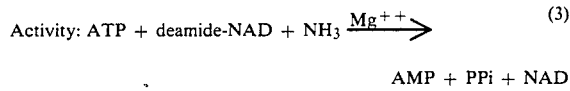
$$\text{Activity: ATP + deamide-NAD + NH}_3 \xrightarrow{Mg^{++}} \text{AMP + PPi + NAD} \quad (3)$$

(4) Substrate specificity: NH₃, L-Gln, L-Asn,

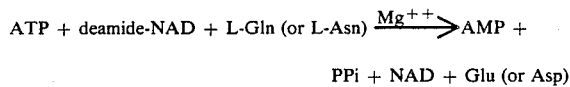
$$\text{ATP + deamide-NAD + L-Gln (or L-Asn)} \xrightarrow{Mg^{++}} \text{AMP + PPi + NAD + Glu (or Asp)}$$

(5) Optimum pH:
Reaction medium I, identified hereinafter under the assay method for enzymatic activity, is mixed with acetate buffer (pH 3.8–6.6), dimethylglutarate-NaOH buffer (pH 5.1–6.8) and Tris-HCl buffer (pH 6.5–8.8), and the enzyme activity is measured. As shown in FIG. 1, the optimum pH is pH 8.0–8.7.

Figure 2:
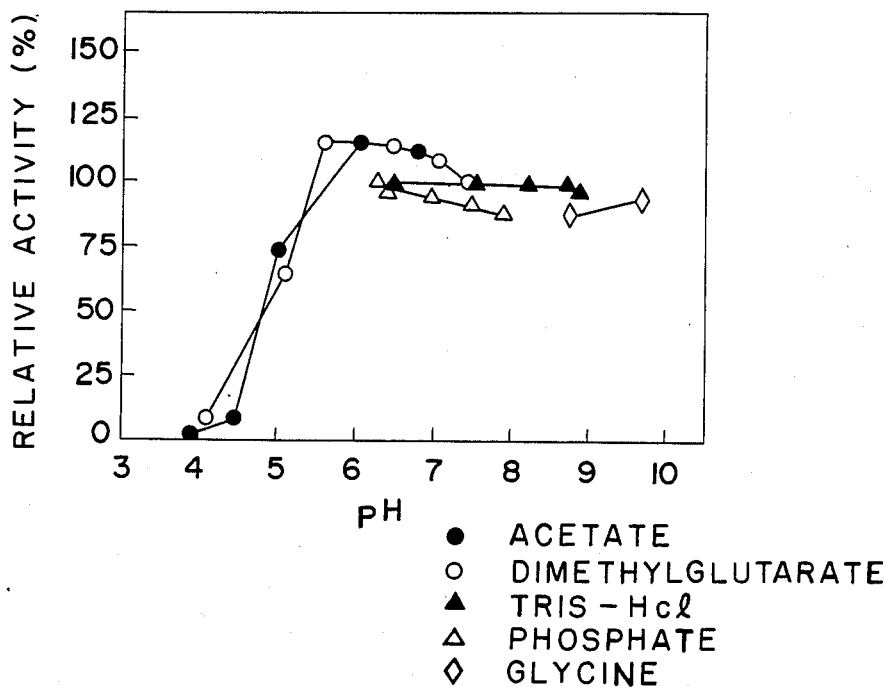
FIG. 2 is the curve of pH-stability.

(6) pH-stability:
The enzyme is dissolved in 50 mM acetate buffer (pH 3.9–6.8), dimethylglutarate-NaOH buffer (pH 4.1–7.1), phosphate buffer (pH 6.3–7.9) or Tris-HCl buffer (pH 6.4–8.9), and the solution is incubated at 37° C. for 60 minutes. The remaining enzyme activity is measured by means of an assay method of enzyme activity. The results are shown in FIG. 2 and the enzyme is stable at pH 5.5–9.0.

Figure 3:
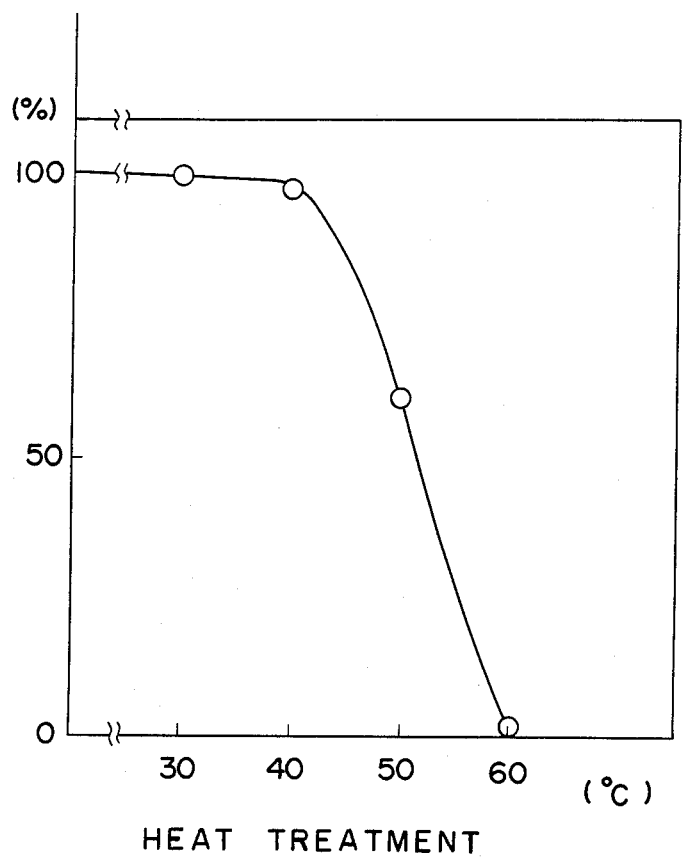
FIG. 3 is the curve of heat-stability.

(7) Heat stability:
The enzyme dissolved in 50 mM Tris-HCl buffer (pH 6.8) is held at various temperature for 10 minutes each, and the remaining enzyme activity is measured. The results are shown in FIG. 3 and the enzyme is stable up to 40° C.

(8) Effect of surface active agent:
In the enzyme activity assay, each surface active agent in Table 1 is added separately to the reaction medium I, the mixture is heated at 37° C., and the enzyme solution (5 μl) is added therein. The mixture is incubated at 37° C. for 10 minutes, then the reaction medium II identified hereinafter (0.8 ml) is added therein, the mixture is incubated at 37° C. for exactly 5 minutes, and 0.1N HCl (2.0 ml) is added to stop the cycling reaction. The mixture is colorimetrically measured. The results are shown in FIG. 1, and the enzyme is inhibited by cationic and anionic surface active agents.

TABLE 1

| Surface Active Agent | Relative Activity (%) |
|---|---|
| No addition | 100 |
| Adekatol SO-120 (Polyoxyethylene secondary straight chain alcohol ethoxylate) | 108.2 |
| Adekatol SO-145 (Polyoxyethylene secondary straight chain alcohol ethoxylate) | 106.9 |
| Brig 35 (Polyoxyethylene (23) lauryl alcohol | 107.5 |
| Cation DT-205 (N—methyl-N—fatty acid-N,N′,N′—tris(polyoxyethylene-N′—methylpropylene-diammonium chloride | 10.5 |
| Cation FB (Alkyl trimethyl ammonium chloride) | 11.8 |
| Cetylpyridinium chloride | 1.6 |
| Sodium dodecyl sulfate | 2.3 |
| Tween-80 (Polyoxyethylene (20) sorbitan monooleate | 102.3 |
| Cholate | 105.6 |

TABLE 1-continued

| Surface Active Agent | Relative Activity (%) |
|---|---|
| Cetyl trimethyl ammonium chloride | 4.2 |
| Span 85 (Sorbitan trioleate) | 104.6 |
| Sodium laurylbenzene sulfonate | 6.5 |

(9) Effect of metal ion:
Each metallic salt is added to the reaction medium I (20 mM, containing MgCl₂), which is adjusted up to 1 ml, and the relative activity is measured. The results are shown in Table 2.

TABLE 2

| Metal Salt | Relative Activity (%) |
|---|---|
| No addition | 100 |
| NiCl₂ | 1.06 |
| BaCl₂ | 106 |
| SnCl₂ | 99.3 |
| AlCl₃ | 94.96 |
| CdSO₄ | 2.4 |
| MnCl₂ | 18.2 |
| CuCl₂ | 3.6 |
| ZnCl₂ | 5.3 |
| CoCl₂ | 94.2 |
| MgCl₂ | 102 |
| PCMB | 0.3 |
| CaCl₂ | 103 |

(10) Assay method of enzyme activity:
Enzyme activity assay:
Reaction medium I.
50 mM Tris-HCl buffer pH 8.0
20 mM KCl
20 mM MgCl₂
0.05% bovine serum albumin
2 mM ATP
0.5 mM deamide-NAD
25 mM (NH₄)₂SO₄
Reaction medium II.
50 mM Tris-HCl buffer pH 8.0
10 U diaphorase (Toyo Jozo Co. from genus Bacillus)
3% ethanol
10 U alcohol dehydrogenase/ml (Toyo Jozo, yeast)
0.025% NTB (nitrotetrazolium blue)
0.1% Triton X-100
10 mM EDTA Reaction medium I (0.2 ml) in a test tube is preincubated at 37° C., and the enzyme solution (5 μl) is added therein, then the mixture is incubated at 37° C. for exactly 10 minutes.
Reaction medium II (0.8 ml) is added thereto to stop the reaction and simultaneously to start the cycling reaction at 37° C. for exactly 5 minutes. After stopping the cycling reaction by adding 0.1N-HCl (2.0 ml), the absorbency at 550 nm is measured to calculate the enzyme activity. The enzyme activity is calculated by the following equation:

$$\text{NAD synthetase activity (mU/ml)} = \frac{\Delta A_{550}}{\Delta S_{550}} \times \frac{1.0}{0.005} \times \frac{f}{10}$$

wherein
ΔA: absorbency of specimen,
ΔS: absorbency of standard solution (0.1 mM NAD),
0.005: specimen volume (ml),
10: reaction time,
f: dilution ratio.

The following examples illustrate the present invention but are not to be construed as limiting:

EXAMPLE 1

A liquid medium (pH 7.3, 20 lit.) consisting of peptone 1%, meat extract 1%, yeast extract 0.2% and NaCl 0.3% in a 30 l. jar fermenter was sterilized at 120° C. for 20 minutes. A previously-cultured seed-culture medium of the same composition (200 ml) was inoculated therein and the mixture was cultured at 50° C. for 16 hours with aeration of 20 l/min. and agitation of 300 r.p.m. After cultivation, the cells were collected by centrifugation, and were suspended in 10 mM Tris-HCl (pH 8.0, 2 lit.) containing 0.1% lysozyme, and the medium was incubated at 37° C. for 30 mins. to lyse the cells. The lysed solution was centrifuged at 5,000 r.p.m. for 10 mins. to obtain a supernatant solution (1.0 lit.) Ammonium sulfate was added therein to fractionate the solution (0.44–0.54 saturation) and the obtained precipitate, dissolved in 10 mM Tris-HCl buffer (200 ml, 473 U), was dialyzed against the same buffer (12 lit.) The precipitated insolubles were removed by centrifugation (12,000 r.p.m., 10 min.) The supernatant solution (462 U) was charged on a column (5×30 cm) of DEAE-Sepharose CL-6B buffered with 10 mM Tris-HCl buffer (pH 8.0) and eluted with a gradient of 0–0.5M NaCl. The fractions eluting with 0.15–0.2M NaCl were collected (120 ml, 399 U), concentrated by ultra-filtration using a membrane PM-10 (Amicon Co.), chromatographed with Sephadex G-150 (3.6×80 cm) and the active fractions collected to obtain the purified solution (80 ml, 324 U).

Bovine serum albumin, glucose, maltose, mannitol, sucrose and fructose were added thereto each up to 1% concentration and the material was lyophilized. The lyophilized produce with the above stabilizer added is stable without decrease of activity, whereas the enzyme without the stabilizer added decreased in activity to 86%.

EXAMPLE 2

Reaction medium I:
50 mM Tris-HCl buffer pH 8.0
20 mM KCl
20 mM $MgCl_2$
0.05% bovine serum albumin
1 mM deamide-NAD
50 mM $(NH_4)_2SO_4$
400 mU NAD synthetase/ml Reaction medium II:
50 mM Tris-HCl buffer (pH 8.0)
20 U diaphorase/ml
3% ethanol
20 U alcohol dehydrogenase/ml
0.05% NTB
0.1% Triton X-100

Reaction mixture I (0.2 ml) in a test tube was preincubated at 37° C., and 0, 5, 10, 20, 30 and 40 μM ATP solutions (5 μl each) were added thereto, respectively; then each was incubated at 37° C. for 10 minutes. Reaction medium II (0.3 ml) was added therein, and each was incubated at 37° C. for exactly 5 minutes, whereupon the reaction was stopped by adding 0.1N-HCl (2.0 ml) and the absorbency was measured at 550 nm. The results are shown in FIG. 4. As shown in that figure, good linearity was obtained. The cycling rate is 4,800 per hour.

EXAMPLE 3

Reaction media I and II were mixed in equal proportions and pre-incubated at 37° C. The mixture (1.0 ml) was put into a spectrophotometer quartz-cell (1.0 ml) set at 37° C., and an ATP solution (5 μl) of the same concentration as in Example 2 was added therein. The absorption every 2 minutes from 5–7 minutes after addition of ATP was measured at 550 nm. As shown in FIG. 5, good linearity with high sensitivity was observed by the kinetics assay method. The cycling rate was approximately 2,800 per hour.

EXAMPLE 4

50 mM $(NH_4)_2SO_4$ in the reaction medium I in Example 2 was replaced by 5 mM ATP to prepare the reaction medium. Various concentrations of ammonium sulfate, L-gln or L-asp were added thereto and treated the same way as in Example 2. As shown in FIG. 6, good linearity was obtained for ammonium sulfate, L-gln and L-asp.

What is claimed is:

1. A biologically pure culture of *Bacillus licheniformis* B-0844 FERM P-6809.

* * * * *